(12) United States Patent
Archie

(10) Patent No.: US 7,479,633 B2
(45) Date of Patent: Jan. 20, 2009

(54) METHODOLOGY FOR CRITICAL DIMENSION METROLOGY USING STEPPER FOCUS MONITOR INFORMATION

(75) Inventor: Charles N. Archie, Granite Springs, NY (US)

(73) Assignee: International Business Machines Corporation, Armonk, NY (US)

( * ) Notice: Subject to any disclaimer, the term of this patent is extended or adjusted under 35 U.S.C. 154(b) by 1070 days.

(21) Appl. No.: 09/902,374

(22) Filed: Jul. 10, 2001

(65) Prior Publication Data

US 2003/0010912 A1    Jan. 16, 2003

(51) Int. Cl.
*G01N 23/225* (2006.01)
(52) U.S. Cl. ............ 250/310; 250/307; 118/63
(58) Field of Classification Search .......... 250/310
See application file for complete search history.

(56) References Cited

U.S. PATENT DOCUMENTS

| | | | |
|---|---|---|---|
| 5,621,652 A | 4/1997 | Eakin | |
| 5,914,784 A | 6/1999 | Ausschnitt et al. | |
| 5,969,273 A | 10/1999 | Archie et al. | |
| 6,054,710 A | 4/2000 | Bruggeman | |
| 6,063,531 A | 5/2000 | Shingh et al. | |
| 6,140,644 A | 10/2000 | Kavanami et al. | |
| 6,185,323 B1 | 2/2001 | Archie et al. | |
| 6,287,876 B1 * | 9/2001 | Fujiwara | 438/4 |
| 6,388,253 B1 * | 5/2002 | Su | 250/310 |
| 6,616,759 B2 * | 9/2003 | Tanaka et al. | 118/63 |

* cited by examiner

*Primary Examiner*—David A. Vanore
*Assistant Examiner*—Phillip A. Johnston
(74) *Attorney, Agent, or Firm*—Gibb & Rahman, LLC; Todd M. C. Li, Esq.

(57) ABSTRACT

A method of producing an accurate critical dimension measurement comprises navigating to a critical dimension structure, performing a scanning electron microscope focusing, performing a final location alignment, acquiring waveform data, analyzing the data to determine an approximate critical dimension, analyzing the data to determine a stepper focus parameter, combining the stepper focus parameter with the critical dimension to generate an accurate critical dimension value, and reporting the same.

26 Claims, 6 Drawing Sheets

METHODOLOGY FOR CRITICAL DIMENSION METROLOGY USING STEPPER FOCUS MONITOR INFORMATION

BACKGROUND OF THE INVENTION

1. Field of the Invention

The present invention generally relates to semiconductor manufacturing processes, and more particularly for improving the accuracy of critical dimension measurement processes.

2. Description of the Related Art

The general environment of semiconductor manufacturing related to lithography and etching has two fundamental components: process control and product compliance. More precisely, in the past, product compliance testing could be accomplished by making a critical dimension (CD) measurement after the lithographic patterning process. When the product failed to comply compared with defined standards, the CD measurement deviation from the target value could be used to change the stepper dose in the rework step. This use of the CD measurement to feed back information to the lithographic process is referred to as process control. To use CD measurements to control the lithography dose requires calibrations. That is, it is necessary to quantitatively determine the correlation between the dosage and the CD.

Currently, patterning processes are much more demanding than previous processes. In order to handle a smaller process tolerance, there are several issues which need to be addressed. The lithography process now has two significant variables that need control: dosage and focus. Furthermore, the use of the resist pattern on the semiconductor substrate wafer in subsequent processing steps (etching, doping, plating, etc . . . ) requires even more structural information, such as the measurement of the resist structure at its bottom, the sidewall angle, and the height of the resist, etc . . .

New demands for compliance monitoring and lithography process control are producing a stream of new innovations. These fall into roughly three categories: better structural measurements for compliance monitoring, better stepper focus and dose monitoring for process control, and techniques that attempt to perform both roles.

Previous critical dimension measurements have been corrupted by structural features, which are not relevant to the critical dimension, but rather are highly sensitive to the stepper focus, like the sidewall angle. Therefore, there is a need for a new method to obtain more accurate critical dimension information by combining the CD measurements with focus monitor information to essentially remove the bias of the undesirable structural components.

Figure 1:
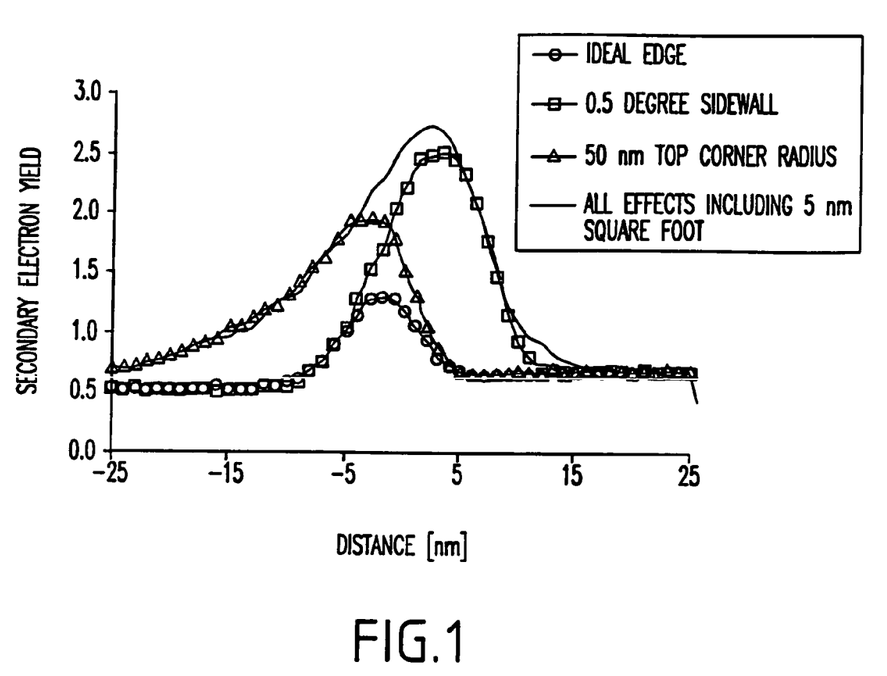
FIG. 1 is a graphical representation of SEM data simulations for printed features with various sidewall structural components.

As illustrated in FIG. 1, using a simulation code, the waveform peaks for edges with various structural elements is calculated. The ideal edge has a sharp top corner, vertical sidewall, and no bottom foot. The cases considered here include a sidewall deviating from vertical by 0.5 degrees, a rounded top corner with a radius of 50 nm, and a small square foot of 5 nm. Some of these changes affect the location of the critical edge, and some do not. However, all affect the waveform.

As mentioned, the control of semiconductor manufacturing processes like lithography and etching requires the ability to measure critical dimensions of features accurately and precisely. The trend to smaller geometries and more complex designs is challenging the capabilities of CD metrology instruments. On the one hand, the best critical dimension scanning electron microscopes (CDSEM) can show an acceptable single tool precision for many manufacturing levels. However, these same tools are failing to accurately measure the changes due to process drifts. This can result in both false positive (passing bad products) and false negative (failing good products) calls, which have serious financial impacts.

Figure 2:
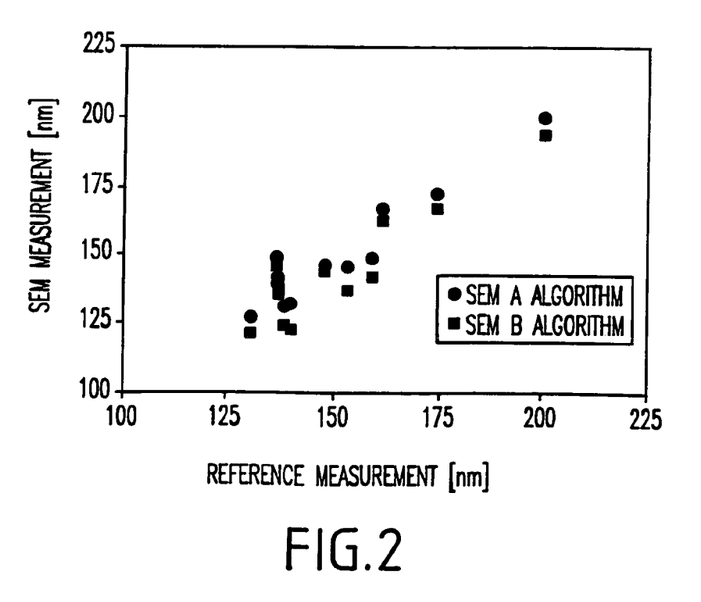
FIG. 2 is a graphical representation of comparing measurements of two CDSEMs with measurements from a reference system.

An example illustrating this problem is associated with FIG. 2. This figure shows CDSEM measurements of a post develop isolated raised structure (line) across a focus-and-exposure matrix (FEM) for two leading CDSEMs versus measurements from a respected reference measurement system (RMS). This is a particularly important geometry and material because it is similar to a key semiconductor processing step that determines the speed with which transistors can switch (microprocessor gate level). Tighter and more accurate control at this step of manufacturing can produce computer chips that are extremely fast and profitable. In this case, the RMS is a 2D scanning atomic force microscope (AFM). The AFM measurements identify the critical edge point as the bottom of the structure.

Ideally the data should lie along a straight line with unity slope and zero offset. The scatter of the data around the best fit line is an important measurement quality captured by a quality metric called nonlinearity. Quantitatively, this is proportional to the variance of the scatter. The nonlinearity is normalized such that if all of the variance is due to the random measurement variance measured by reproducibility, then the nonlinearity equals unity. In this case, both CDSEMs have nonlinearities greater than 100. Both are disturbingly large numbers. The single tool precisions for these two CDSEMs are 1.5 nm and 1.8 nm, respectively. Those skilled in the art recognize that, currently, the necessary precision needed for isolated line control is 1.8 nm. The two instruments appear to satisfy this precision requirement but they fail to accurately track the critical dimension changes on the FEM.

Figure 3:
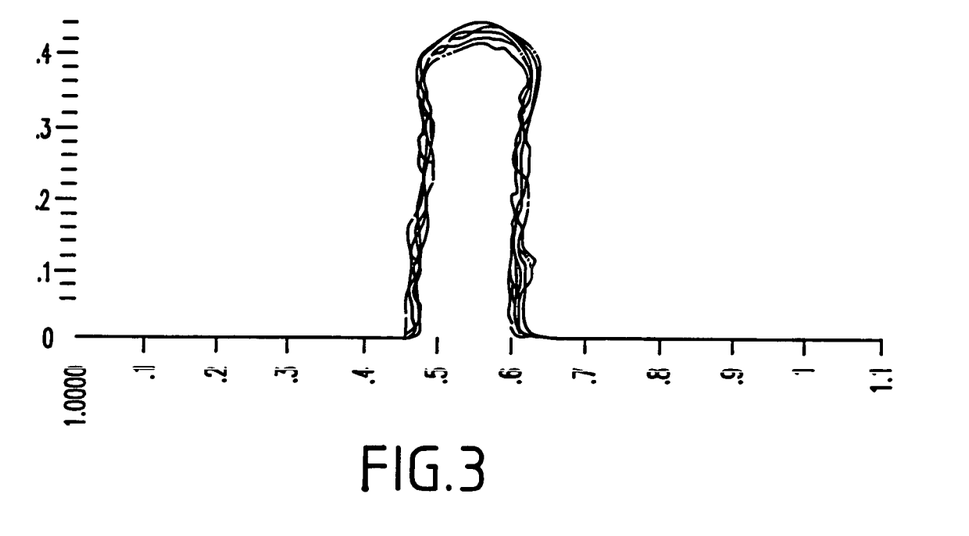
FIG. 3 is a graphical representation of the linescans taken from an atomic force microscope.

In the particular example of the resist isolated line, the problem is associated with severe resist loss during the printing process. This can have profound changes to the line shape. FIG. 3 shows AFM linescans for one of the features on this FEM wafer. The AFM linescans show edge roughness, and even undercut.

Figure 11:
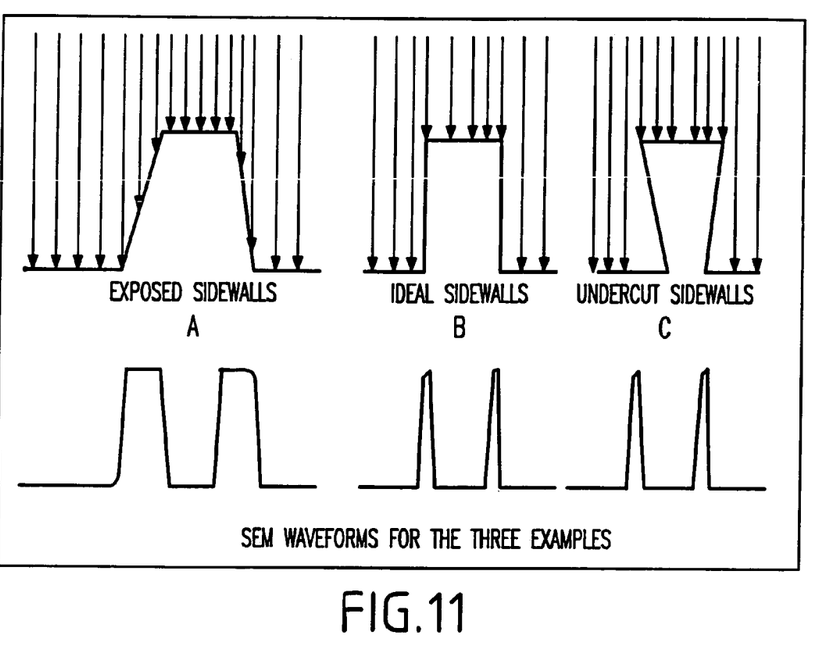
FIG. 11 is a graphical representation of SEM waveforms for various geometries.

These AFM line scans illustrate some of the problems confounding the conventional CDSEM measurement. Typically, the CDSEM directs the electron beam vertically downward on the feature. The beam enters only a small distance into the sample producing secondary electrons, some of these escape the sample and are detected. The basic CDSEM data, called a waveform or linescan, is this detected secondary electron signal versus a primary electron scan position. It is important to note that portions of the feature geometry that are shielded from the electron beam will not be detected. This is illustrated FIG. 11 where cross sections of possible geometries are illustrated. The vertical arrows represent the electron beam hitting the exposed surfaces as it is scanned over the sample. Ideally, the sidewalls should be vertical with sharp corners at the top and bottom. Sometimes the printed feature has undercut sidewalls where the SEM waveform is nearly the same as in the case of ideal sidewalls. Conventional methodologies would falsely report the basewidth measurement of case C the same as case B. The AFM linescans are trusted measurements of the actual feature cross section. The actual AFM linescans of FIG. 3 show an undercut feature with further additional features that can also confuse conventional algorithms.

Figure 4:
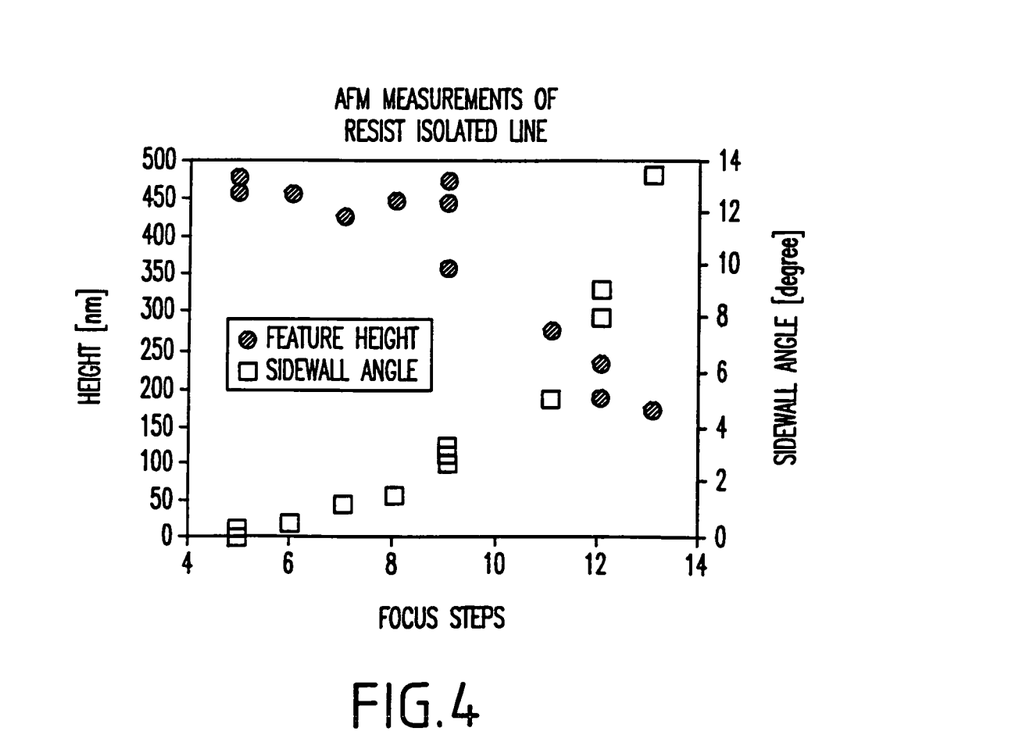
FIG. 4 is a graphical representation of measurements taken from an atomic force microscope.

FIG. 4 shows the variation in feature height and sidewall angle across the FEM, inherent in the prior art approaches. The horizontal axis provides for the stepper focus setting. As shown on the graph, across this FEM, the feature height changes by a factor of three, from approximately 450 nm to 150 nm. There is a significant sidewall angle variation as well, measuring from approximately 0° to almost 14°.

The multiple simultaneous feature changes as a function of stepper focus pose significant challenges for the CD algorithm. Normally, it is the basewidth of the feature that should be reported. These additional changes in the feature geometry should be ignored in the measurement process (data gathering and analysis).

Figure 5:
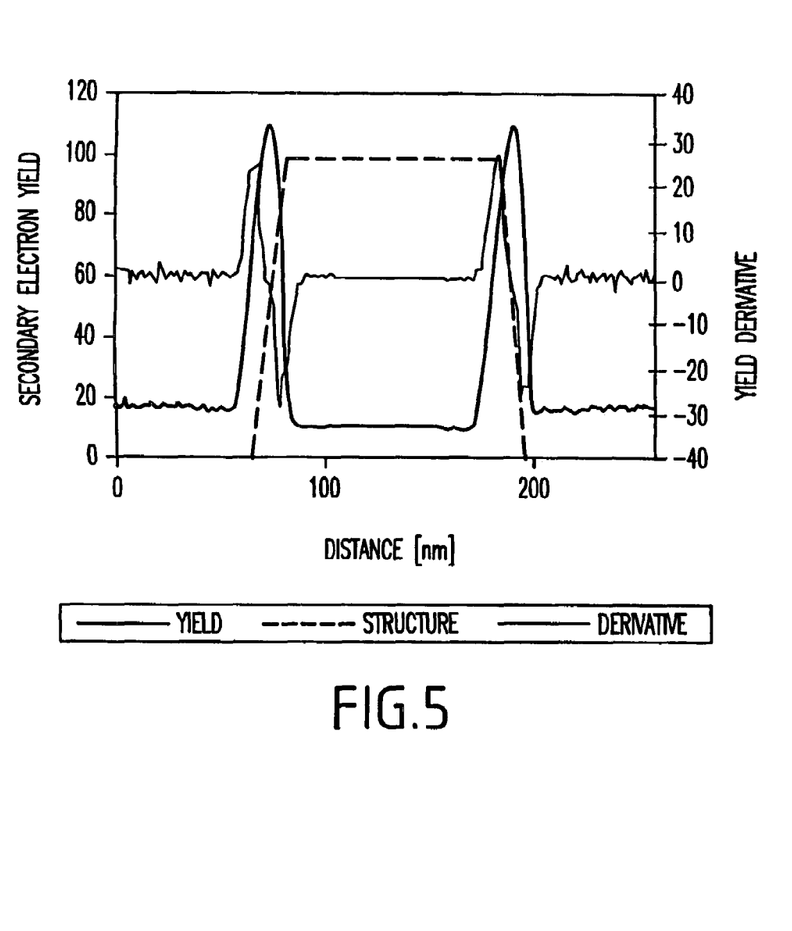
FIG. 5 is a graphical representation of a prior art simulation.

The fundamental assumption underlying the CD measurement is that the location of the true edge of a structure on the semiconductor wafer is associated with some feature or property of the data acquired by the CD measuring instrument. In the case of the CDSEM, the data is usually a one-dimensional waveform or linescan resulting from detecting the secondary electrons generated by sweeping a primary electron beam across the structure. Monte Carlo simulations have indicated that the edge base of the structure (usually identified as the critical edge location) is associated with the outside maximum or minimum slope of the waveform as illustrated in FIG. 5, which was generated using the following parameters: electron beam conditions: 500 eV landing energy, and 10 nm spot size.

This figure shows the results from a prior art Monte Carlo simulation program, Monsel-II. The SEM detected signal is approximately proportional to the secondary electron yield. The SEM operates by scanning the structure from above. The trapezoidal example structure is shown in dotted lines from a side view. Notably, when the primary beam is traversing the left or right edge of the structure there is an increase in the secondary electron yield. With this simplified model of the printed pattern, the derivative of the secondary electron yield shows peaks closely associated with the base of the trapezoidal structure. A common prior art method reports the distance between these outer extreme slope locations as the critical dimension of the structure.

Currently, more and less sophisticated methods are available on most CDSEMs. Generally, they focus on analyzing the signal peak for each edge in some manner. For example, a threshold method could allow the user to define a percentage intensity along the outside portion of the peak to declare as the structure critical edge location. The extreme slope locations may correspond to approximately a 50% threshold. In order to overcome signal-to-noise issues, some methods fit portions of the peak to a functional form and then use a user-selectable threshold to determine the critical edge point.

Another reason to use a greater portion of the peak waveform data and to increase the flexibility for choosing the critical edge point location is to be able to handle the real manufacturing problems of resist footing, corner rounding, edge roughness, and more. These more flexibly defined methods are empirical in nature and a calibration exercise of some sort is necessary to set the parameters. Despite these complications, the operating paradigm is that somewhere in the waveform there is a feature associated with the true critical edge location. This could be called the true-critical-edge paradigm.

Together with the true-critical-edge paradigm there is another common assumption used in selecting the operating conditions and method parameters. This assumption is that the measurement system (beam conditions and method settings) should be optimized to give the smallest single tool precision and smallest measurement offset to a respected reference measurement system. This second assumption has been recently challenged as not emphasizing accuracy enough. In any case, the goal of the prior art is to optimize the measurement system in some manner where the method available has been developed under the assumption of the true-critical-edge paradigm.

Optimizing for minimum precision and even the smallest offset actually are deviations from the true-critical-edge paradigm. This is because selecting method parameters to improve the precision may shift the point in the waveform to associate with the edge away from the true edge to a location with better signal stability. Furthermore, to shift the point in the waveform in order to minimize the offset ignores a very significant offset introduced by the physics of the SEM operation. Nevertheless, the practitioners of this methodology generally ignore the corruption of the true-critical-edge paradigm when performing these compromises as these are generally thought of as minor adjustments. That is, the thinking is that the selected point in the waveform chosen should still be a satisfactory mimic of the true edge location.

Other prior art approaches, such as the Davidson approach (J. S. Villarrubia, A. E. Vladar, J. R. Lowney, M. T. Postek, Jr., "Edge determination for polysilicon lines on gate oxide", Proceedings of SPIE 2001, Volume 4344, Paper 4344-21), to be published, have made a notable exception to this paradigm. By using a unique SEM simulation code, a library of waveforms can be generated corresponding to sample geometries and materials as well as SEM operating conditions. These can then be searched at the time of measurement to identify the best match. The system then reports the critical dimension associated with this best match. Unfortunately, this approach may prove to be too background intensive and has not yet demonstrated an adequate ability to deal with sample charging.

SUMMARY OF THE INVENTION

In view of the foregoing and other problems, disadvantages, and drawbacks of the conventional critical dimension measurement systems, the present invention has been devised, and it is an object of the present invention to provide a method for obtaining more accurate critical dimension information by combining CD measurements from a scanning electron microscope (SEM) with additional information coming from a measurement that is sensitive to stepper focus error. This stepper focus information may come from a separate instrument dedicated to stepper focus monitoring; or a separate measurement on the same CD SEM, which may be using a target optimized to be sensitive to stepper focus; or from the same CD SEM measurement episode by analyzing the data differently from the CD measurement.

In order to attain the object suggested above, there is provided, according to one aspect of the invention, a method of producing an accurate critical dimension measurement value comprising: navigating to a critical dimension structure, performing a scanning electron microscope focus, performing a final alignment of printed pattern and the electron beam, acquiring data by scanning the electron beam across the printed pattern (waveform), analyzing the data, determining an approximate critical dimension, determining a stepper focus parameter, combining the stepper focus parameter with the critical dimension, and generating an accurate critical dimension value, and reporting the same.

BRIEF DESCRIPTION OF THE DRAWINGS

The foregoing and other objects, aspects and advantages will be better understood from the following detailed description of a preferred embodiment(s) of the invention with reference to the drawings, in which.

DETAILED DESCRIPTION OF PREFERRED EMBODIMENTS OF THE INVENTION

As mentioned above, there is a need for a new method to obtain more accurate critical dimension information by combining the CD measurements with focus monitor information to essentially remove the bias associated with undesirable structural components. Thus, in view of the problems associated with the prior art, the ideal CD method should ignore all secondary characteristics and determine solely the distance between critical edge locations. Specifically, a more powerful and accurate paradigm is to acknowledge that multiple structure components contribute to the waveform. In fact, multiple parts of the physical structure can contribute to each point in the waveform and its derivatives. In other words, the true critical edge location could be concealed under a multitude of other phenomena present in the waveform.

According to this paradigm more information is needed to extract the critical dimension information from the waveform. This information could come from other measurement instruments, other measurements performed by the given CD instrument, or even a different analysis of the given waveform. The last two methods are of particular interest since they allow the total determination of the critical dimension to be done solely by one instrument.

Figure 6:
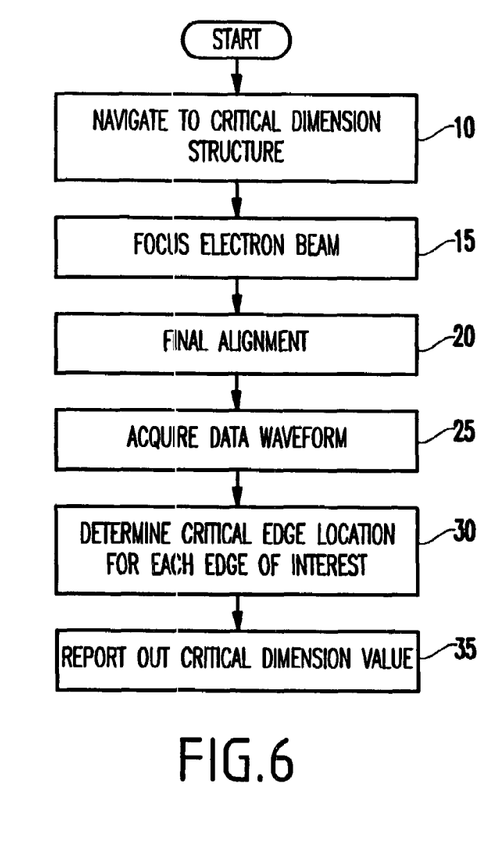
FIG. 6 is a flow diagram illustrating a prior art method.

A flowchart of the prior art method is shown in FIG. 6. In this prior art approach, the method of producing a CD measurement value encompasses the following steps, beginning with navigating to a critical dimension structure 10, focusing an electron beam 15, preparing a final alignment of the electron beam 20, acquiring a waveform of the data generated 25, determining the critical edge location for each edge of interest 30, and reporting the critical dimension value 35.

Figure 7:
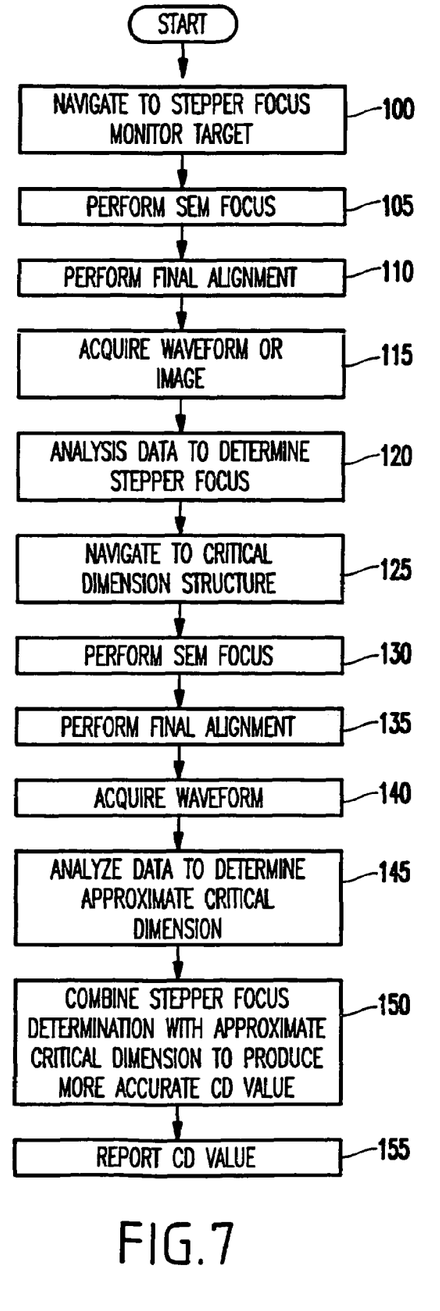
FIG. 7 is a flow diagram illustrating the method according to the present invention.

The first embodiment of the invention uses a separate stepper focus monitor as shown in FIG. 7. In this embodiment, the method provides for first navigating to a stepper focus monitor target 100. Second, a scanning electron microscope focus 105 is performed. Then, a final location alignment 110 is performed. Next, a waveform or image data set of the focus target 115 is acquired. Following this step, the data is analyzed in order to determine a stepper focus 120. The next step is navigating to a critical dimension structure 125. Then, a scanning electron microscope focus 130 is performed as is a final location alignment 135. Next, a waveform 140 is acquired, which results in analyzing the data in order to determine an approximate critical dimension 145. After which, the stepper focus determination is combined with the approximate critical dimension to produce a more accurate CD value 150. Finally, the CD value is reported 155.

What distinguishes the present invention from the prior art is the realization that the prior art CD measurements have been corrupted by structural features not relevant to the critical dimension but which are highly sensitive to stepper focus, like sidewall angle. In order to ameliorate this situation, the prior art CD measurement must be combined with focus monitor information to essentially remove the undesirable component. The inventive aspects of the present invention involve fixing the CD measurement accuracy. This combination may be accomplished using a separate stepper focus monitor as described above, or using embedded stepper focus information, which is described next.

Figure 8:
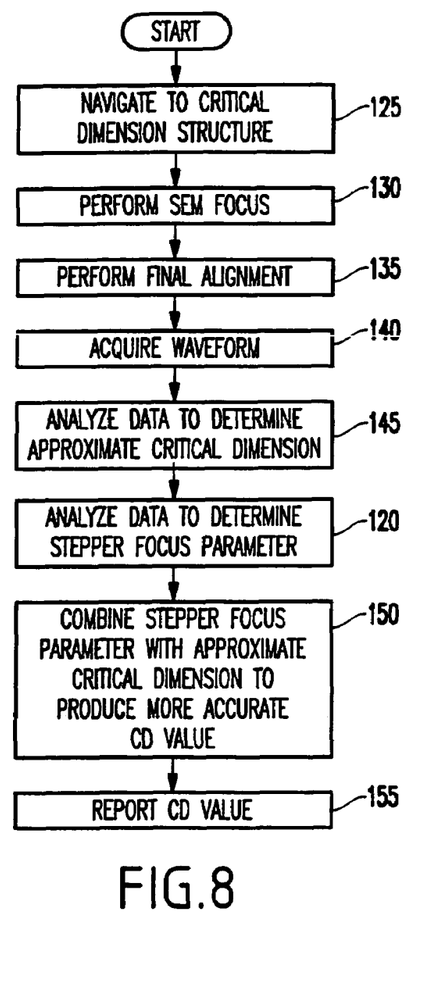
FIG. 8 is a flow diagram illustrating a preferred method of the present invention.

The preferred embodiment of the new paradigm, with a combined analysis of a single waveform of the critical dimension structure, is illustrated in FIG. 8. It is similar to the methodology outlined in FIG. 7, but with a more streamlined approach whereby, the first step is navigating to a critical dimension structure 125. Then, a scanning electron microscope focus 130 is performed, as is a final location alignment 135. Next, a waveform 140 is acquired, which results in the data being analyzed in order to determine an approximate critical dimension 145. At this stage, the method provides for analyzing the data in order to determine the stepper focus parameter 120. After which, the stepper focus parameter is combined with the approximate critical dimension to produce a more accurate CD value 150. Finally, the CD value is reported 155.

Once again, what distinguishes the present invention from the prior art is the understanding that CD measurements inherent in the prior art are essentially corrupted due to consideration of structural characteristics, which are not relevant to the critical dimension, but which are highly sensitive to the stepper focus, such as sidewall angle. Fixing this problem leads to the present invention, whereby the prior art CD measurement is combined with focus monitor information in order to remove the undesirable component. This fixes the CD measurement accuracy, and can be accomplished using separate or embedded stepper focus information.

In the example of FIG. 2, the large nonlinearities are signatures of poor accuracy. This situation can be considerably improved by including knowledge of the stepper focus in the determination of the critical dimension value. In the case of this FEM the actual stepper focus is known for each exposure field. Using stepper focus and the RMS values, the SEM measurements can fit in a two variable linear regression by determining best fit parameters A, B, and C such that $$[CD_{old}] = A \times [CD_{rms}] + B \times [\text{Focus}] + C$$

This equation is meant to convey that coefficients A, B, and C are determined by performing a linear regression with data set of $[CD_{old}]$, $[CD_{rms}]$, and [Focus].

Figure 9:
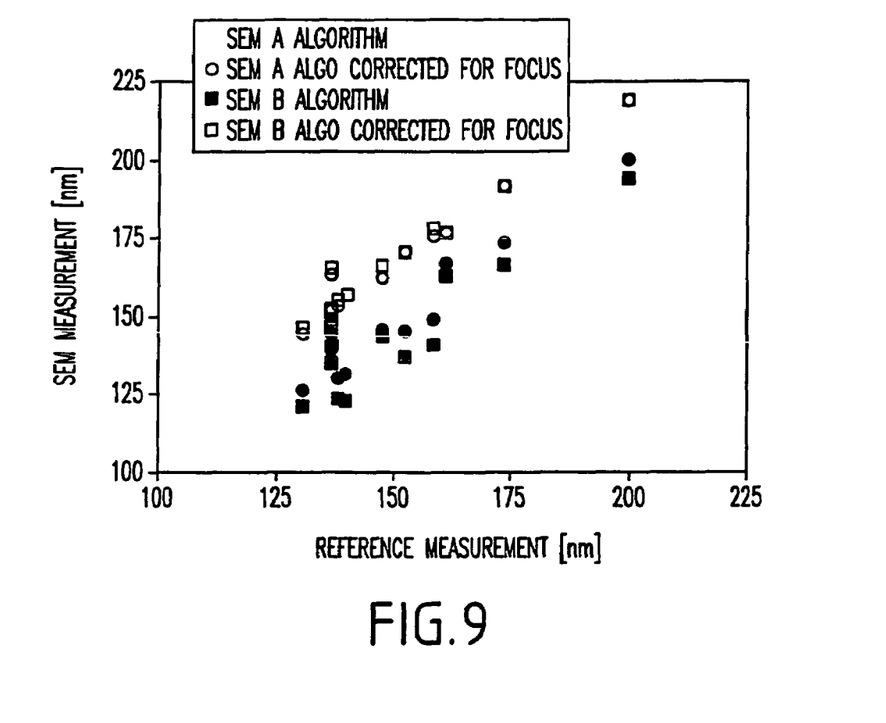
FIG. 9 is a graphical representation of two CDSEMs measurements using prior art algorithms and corrected measurements using known stepper focus compared to measurements from a reference system.

To graphically show the improvement, FIG. 9 illustrates a plot of the original data of FIG. 2 along with the modified data of $[CD_{old} - (B \times \text{Focus})]$ for each CDSEM. As shown, the improvement in linearity is dramatic. Even the one data point for each SEM that continues to be significantly away from the linear trend is noteworthy; as this is the case shown in FIG. 2, the only recursive structure measured on the FEM wafer. The nonlinearities fall below twenty by using this additional information and they drop below five if the one recursive structure is eliminated from the data sets. The nonlinearity metric is dimensionless.

This then leads to the first method embodiment of the new paradigm according to the present invention. The first step is to use the CDSEM to make two measurements: one, a stepper focus monitor and the other, a conventional $CD_{old}$ measurement. The calibration (fitting) exercise just described provides coefficients A, B, and C which are used to determine the new $CD_{new}$ measurement:

$$CD_{new} = \frac{[CD_{old} - (B \times Focus) - C]}{A}$$

The preferred embodiment method uses the same waveform obtained for the conventional CD method as the data for a stepper focus monitor. Generally, this is using a different portion of the waveform or a different filtering of the data to obtain a stepper focus measurement than what was used for the conventional CD measurement. This focus measurement is then used in the same way as previously described to provide a new CD measurement with significantly improved accuracy. Changes to the waveform coming from sidewall angle changes, top corner rounding, or even resist foot changes are possible candidates for sensitive stepper focus monitors.

Figure 10:
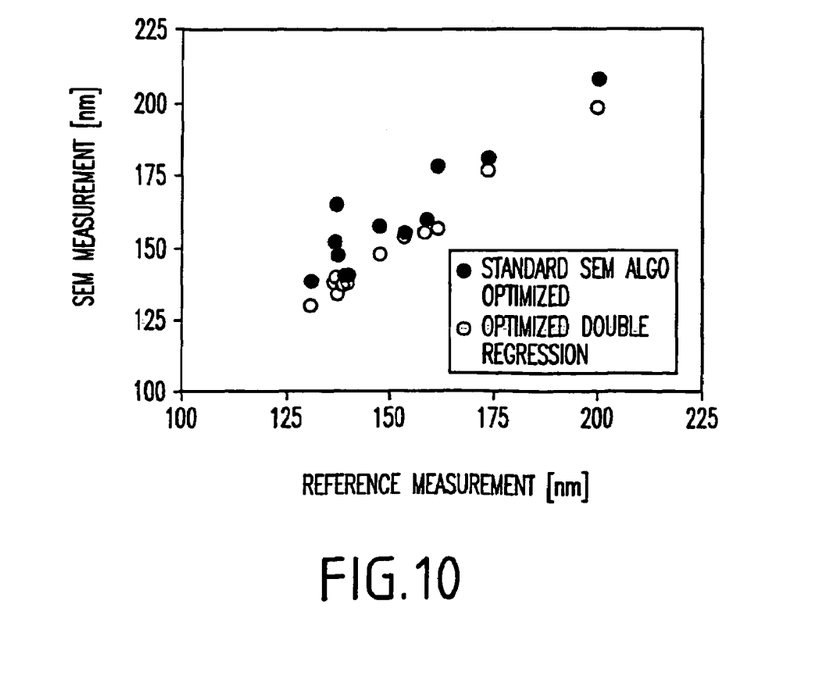
FIG. 10 is a graphical representation of CDSEM measurements comparing prior art and the preferred method of the present invention.

FIG. 10 shows an example of this preferred embodiment method. Here, the conventional method reports a CD measurement based on finding a location near the bottom of the peak for each edge. The new method uses this measurement and the edge width as a focus monitor. The optimal fit in this instance is given by:

$$CD_{new} = [(0.69 \times CD_{old}) + (2.15 \times Edge\ Width) - (66\ nm)]$$

It should be emphasized that the optimum combination of old critical dimension measurements and focus monitor (here, edge width) is not seeking out the true critical edge location, but rather a value that best mimics the changes in critical dimension as a function of stepper focus and dose.

In fact, since the geometric point indicated by the optimal combination is more than 30 nm beyond the critical edge location determined by the old method, this requires the new method to have an offset correction, as indicated, of 66 nm. Note, this is a specific example of the preferred embodiment method. An important function of the invention is combining stepper focus and the old method CD measurement and their coefficients need to be determined by a calibration exercise.

As previously mentioned, the conventional CDSEM systems are overly sensitive to structural changes not associated with the critical dimension. These in turn are affected by the stepper focus, so the conventional method has an undesirable dependency on the stepper focus. The old method based on the old paradigm is a good first approximation, and the inventive inclusion of the stepper focus information is a significant correction. As a significant correction, the functional form will generally be linear, but in some circumstances could be quadratic, with respect to focus. This needs to be explored for each application during a calibration exercise.

The open circles in FIG. 10 show the CD measurements using the preferred embodiment of this invention while the closed circles show the best prior art CD measurements. Even without calculating the nonlinearity metric for each case it is obvious that the preferred embodiment measurements are much better linearly correlated with the reference measurements from the RMS.

The task of implementing the present invention is simplified somewhat because while the possible changes to the structure are many, the main sources for such changes are usually only two: stepper focus and stepper dose. Those skilled in the art can readily see that if and when additional qualitative new sources for structural change become important, then this approach can be augmented in an obvious way. This means that the multiple changes described by FIG. 4 versus stepper focus are correlated; i.e., they occur together. Of course, the exact nature of the correlation depends on many properties of the resist system and lithography conditions that should be fairly static for a particular process; the resist property called gamma, the degree of coherence for the stepper illumination, etc. However, because of these dependencies, proper use of a method based on the new paradigm may require recalibration whenever a significant change is made to the manufacturing process.

As previously mentioned, what distinguishes the present invention from the prior art is the understanding that CD measurements inherent in the prior art are essentially corrupted due to consideration of structural characteristics, which are not relevant to the critical dimension, but which are highly sensitive to the stepper focus, such as sidewall angle measurements. Fixing this problem leads to the present invention, whereby the prior art CD measurement is combined with focus monitor information in order to remove the undesirable component. This fixes the CD measurement accuracy, and can be accomplished using separate or embedded stepper focus information.

The benefits of the present invention include the following: more accurate critical dimension measurements reduce the frequency of false positive (passing bad product) and false negative (failing good product) calls in dispositioning of product during manufacturing. This leads to cost savings (less rework) and more profit (more yield).

While the discussion has centered on an isolated raised structure of resist, the principles of the new paradigm are general with respect to geometry and materials. Moreover, while the invention has been described in terms of preferred embodiments, those skilled in the art will recognize that the invention can be practiced with modification within the spirit and scope of the appended claims.

What is claimed is:

1. A method of producing an optimum critical dimension value, said method comprising:

acquiring a waveform of data for a critical dimension structure;

determining a stepper focus parameter for said critical dimension structure;

calculating an approximate critical dimension measurement for said critical dimension structure;

calibrating said data of said waveform by determining at least three best fit data parameters for improving a linearity of said waveform;

combining said stepper focus parameter with said approximate critical dimension measurement and said best fit data parameters, wherein said combining removes structural bias parameters from said approximate critical dimension measurement; and generating said optimum critical dimension value from said combining, wherein said optimum critical dimension value comprises structural measurements of said critical dimension structure that are only relevant to a critical dimension of said critical dimension structure.

2. The method of claim 1, wherein said determining comprises:
   navigating to a stepper focus monitor target;
   performing a scanning electron microscope focusing; and
   performing a final alignment of said target.

3. The method of claim 2, wherein said determining further comprises:
   acquiring the waveform data;
   analyzing said waveform data; and
   determining said stepper focus parameter based on said analyzing.

4. The method of claim 2, wherein said determining further comprises:
   acquiring an image data;
   analyzing said image data; and
   determining said stepper focus parameter based on said analyzing.

5. The method of claim 1, wherein said generating comprises:
   navigating to said critical dimension structure;
   performing a scanning electron microscope focusing; and
   performing a final alignment of said critical dimension structure.

6. The method of claim 5, wherein said generating further comprises:
   acquiring the waveform data;
   analyzing said waveform data; and
   determining said optimum critical dimension value based on said analyzing.

7. The method of claim 5, wherein said generating further comprises:
   acquiring an image data;
   analyzing said image data; and
   determining said optimum critical dimension value based on said analyzing.

8. A method of producing an optimum critical dimension value, said method comprising:
   generating a scanning electron microscope focus;
   generating a waveform data based on output from said scanning electron microscope focus;
   analyzing said waveform data to determine an approximate critical dimension measurement;
   calibrating said waveform data by determining at least three best fit data parameters for improving a linearity of said waveform data;
   analyzing said waveform data to determine a stepper focus parameter;
   combining said stepper focus parameter with said approximate critical dimension measurement and said best fit data parameters, wherein said combining removes structural bias from said approximate critical dimension measurement; and
   generating said optimum critical dimension value from said combining, wherein said optimum critical dimension value comprises structural measurements of a critical dimension structure that are only relevant to a critical dimension of said critical dimension structure.

9. The method of claim 8, wherein said generating a waveform data further comprises:
   navigating to a critical dimension structure;
   performing a scanning electron microscope focusing;
   performing a final alignment of said critical dimension structure; and
   acquiring said waveform data based on said scanning electron microscope focusing and said final alignment.

10. A method of producing an optimum critical dimension value, said method comprising:
    generating a scanning electron microscope focus;
    generating an image data based on output from said scanning electron microscope focus;
    analyzing said image data to determine an approximate critical dimension measurement;
    calibrating said image data by determining at least three best fit data parameters for improving a linearity of said image data;
    analyzing said image data to determine a stepper focus parameter;
    combining said stepper focus parameter with said approximate critical dimension measurement and said best fit data parameters, wherein said combining removes structural bias from said approximate critical dimension measurement; and
    generating said optimum critical dimension value from said combining, wherein said optimum critical dimension value comprises structural measurements of a critical dimension structure that are only relevant to a critical dimension of said critical dimension structure.

11. The method of claim 10, wherein said generating an image data further comprises:
    navigating to a critical dimension structure;
    performing a scanning electron microscope focusing;
    performing a final alignment of said critical dimension structure; and
    acquiring said image data based on said scanning electron microscope focusing and said final alignment.

12. A method of producing an optimum critical dimension value, said method comprising:
    acquiring data representative of a critical dimension structure;
    determining a stepper focus parameter for said critical dimension structure;
    measuring an approximate critical dimension measurement for said critical dimension structure;
    calibrating said data by determining at least three best fit data parameters for improving a linearity of said data;
    combining said stepper focus parameter with said approximate critical dimension measurement and said best fit data parameters, wherein said combining removes structural bias parameters from said approximate critical dimension measurement; and
    generating said optimum critical dimension value based on said combining, wherein said optimum critical dimension value comprises structural measurements of said critical dimension structure that are only relevant to a critical dimension of said critical dimension structure.

13. The method of claim 12, wherein said determining comprises:
    navigating to a stepper focus monitor target;
    performing a scanning electron microscope focusing; and
    performing a final alignment of said target.

14. The method of claim 13, wherein said determining further comprises:
    acquiring a waveform data;
    analyzing said waveform data; and
    determining said stepper focus parameter based on said analyzing.

15. The method of claim 13, wherein said determining further comprises:
    acquiring an image data;
    analyzing said image data; and
    determining said stepper focus parameter based on said analyzing.

16. The method of claim 12, wherein said generating comprises:

navigating to said critical dimension structure;
performing a scanning electron microscope focusing; and
performing a final alignment of said critical dimension structure.

17. The method of claim 16, wherein said generating further comprises:
acquiring a waveform data;
analyzing said waveform data; and
determining said optimum critical dimension value based on said analyzing.

18. The method of claim 16, wherein said generating further comprises:
acquiring an image data;
analyzing said image data; and
determining said optimum critical dimension value based on said analyzing.

19. A method of producing an optimum critical dimension value, said method comprising:
acquiring data representative of a critical dimension structure;
determining a stepper focus parameter for said critical dimension structure;
measuring an approximate critical dimension measurement for said critical dimension structure;
calibrating said data by determining at least three best fit data parameters for improving a linearity of said data;
combining said stepper focus parameter with said approximate critical dimension measurement and said best fit data parameters, wherein said combining removes structural bias parameters from said approximate critical dimension measurement; and
generating said optimum critical dimension value based on said combining, wherein said optimum critical dimension value comprises structural measurements of said critical dimension structure that are only relevant to a critical dimension of said critical dimension structure;
wherein said determining further comprises:
navigating to a stepper focus monitor target;
performing a scanning electron microscope focusing at said target;
performing a final alignment of said target based on said scanning electron microscope focusing at said target;
acquiring a first data set from said scanning electron microscope focusing;
analyzing said first data set; and
determining said stepper focus parameter based on said analyzing;
wherein said generating further comprises:
navigating to said critical dimension structure;
performing a scanning electron microscope focusing at said critical dimension structure;
performing a final alignment of said critical dimension structure;
acquiring a second data set from said scanning electron microscope focusing at said critical dimension structure;
analyzing said second data set; and
determining said optimum critical dimension value based on said analyzing.

20. A program storage device readable by a computer, tangibly embodying a program of instructions executable by the computer to perform a method of producing an optimum critical dimension value, said method comprising:
acquiring a waveform of data for a critical dimension structure;
determining a stepper focus parameter for said critical dimension structure;
calculating an approximate critical dimension measurement for said critical dimension structure;
calibrating said data of said waveform by determining at least three best fit data parameters for improving a linearity of said waveform;
combining said stepper focus parameter with said approximate critical dimension measurement and said best fit data parameters, wherein said combining removes structural bias parameters from said approximate critical dimension measurement; and
generating said optimum critical dimension value from said combining, wherein said optimum critical dimension value comprises structural measurements of said critical dimension structure that are only relevant to a critical dimension of said critical dimension structure.

21. The program storage device of claim 20, wherein in said method said determining comprises:
navigating to a stepper focus monitor target;
performing a scanning electron microscope focusing; and
performing a final alignment of said target.

22. The program storage device of claim 21, wherein in said method said determining further comprises:
acquiring the waveform data;
analyzing said waveform data; and determining said stepper focus parameter based on said analyzing.

23. The program storage device of claim 21, wherein in said method said determining further comprises:
acquiring an image data;
analyzing said image data; and
determining said stepper focus parameter based on said analyzing.

24. The program storage device of claim 20, wherein in said method said generating comprises:
navigating to said critical dimension structure;
performing a scanning electron microscope focusing; and
performing a final alignment of said critical dimension structure.

25. The program storage device of claim 24, wherein in said method said generating further comprises:
acquiring the waveform data;
analyzing said waveform data; and
determining said optimum critical dimension value based on said analyzing.

26. The program storage device of claim 24, wherein in said method said generating further comprises:
acquiring an image data;
analyzing said image data; and
determining said optimum critical dimension value based on said analyzing.

* * * * *